United States Patent [19]

Yoshida et al.

[11] Patent Number: 5,163,407
[45] Date of Patent: Nov. 17, 1992

[54] METHOD FOR DETECTING FUEL BLENDING RATIO

[75] Inventors: Masato Yoshida; Takanoa Yokoyama; Muneyoshi Nanba; Yoshihiko Kato; Kazumasa Iida; Katsuhiko Miyamoto, all of Kyoto, Japan

[73] Assignee: Mitsubishi Jidosha Kogyo Kabushiki Kaisha, Japan

[21] Appl. No.: 761,953

[22] PCT Filed: Feb. 14, 1991

[86] PCT No.: PCT/JP91/00178

§ 371 Date: Sep. 23, 1991

§ 102(e) Date: Sep. 23, 1991

[87] PCT Pub. No.: WO91/12424

PCT Pub. Date: Aug. 22, 1991

[30] Foreign Application Priority Data

Feb. 16, 1990 [JP] Japan .................................... 2-35643

[51] Int. Cl.$^5$ ............................................. F02M 51/00
[52] U.S. Cl. .................................... 123/672; 123/114; 123/494; 123/674
[58] Field of Search ............... 123/489, 494, 1 R, 1 A, 123/478, 440; 204/424, 426, 195 S, 1 S; 73/35

[56] References Cited

U.S. PATENT DOCUMENTS

| | | | |
|---|---|---|---|
| 4,419,212 | 12/1983 | Dietz et al. | 204/424 |
| 4,706,629 | 11/1987 | Wineland et al. | 123/1 A |
| 4,706,630 | 11/1987 | Wineland et al. | 123/1 A |
| 4,770,129 | 9/1988 | Myata et al. | 123/1 A |
| 4,967,714 | 11/1990 | Inoue | 123/489 |
| 4,989,570 | 2/1991 | Kuribara et al. | 123/1 A |
| 4,995,367 | 2/1991 | Yamauchi et al. | 123/494 |
| 5,007,398 | 4/1991 | Kashiwabara | 123/479 |
| 5,044,344 | 9/1991 | Tuckey | 123/497 |
| 5,094,208 | 3/1992 | Adam | 123/489 |

*Primary Examiner*—Raymond A. Neill

[57] ABSTRACT

A fuel blending ratio detecting method computes a control blending ratio on the basis of blending ratio information generated from a blending ratio sensor or air/fuel ratio information generated from an O$_2$ sensor, and when the engine is stopped, the control blending ratio detected at that time is stored in a backup memory as a memory blending ratio. At the time of re-starting the engine, the memory blending ratio can be used as the control blending ratio B for a predetermined limited period.

1 Claim, 8 Drawing Sheets

METHOD FOR DETECTING FUEL BLENDING RATIO

TECHNICAL FIELD

This invention relates to a fuel blending ratio detecting method for detecting the blending ratio of a mixed fuel supplied to an internal combustion engine.

BACKGROUND ART

Methanol is now noted as a fuel giving rise to less environmental pollution, and methanol engines are therefore being developed now. However, an immediate change-over of fuel used in all kinds of automotive vehicles from gasoline to methanol is almost impossible, and, at the time of change-over, a situation will occur where at least temporaily both the methanol fuel and the gasoline fuel are used.

With a view to deal with such a situation, an introduction of a vehicle is proposed in which both the gasoline fuel and the methanol fuel can be used, that is, a vehicle which has the degree of freedom with respect to fuel to be used. (Such a vehicle will be referred to hereinafter simply as an FFV.)

In order that the engine of such an FFV can be accurately controlled, the blending ratio which is the mixing ratio of fuel between the gasoline and the methanol is to be continuously detected so as to execute various required controls on the engine. A blending ratio detecting device or a sensor for use in such a purpose has been developed and is now in use which can be directly associated with the fuel feed system of the engine so as to directly detect the blending ratio of the fuel.

There is also a method for detecting the blending ratio by the use of an $O_2$ sensor which generates the information of oxygen concentration in the exhaust gases of an engine, that is, the air/fuel ratio.

However, the practical use of the blending ratio sensor using a conventional photoelectric transducer has had the problems that fouling of its optical system with time must be dealt with, and the sensor cannot operate in its inactive state immediately after the time of engine starting.

On the other hand, in the case of the method using the $O_2$ sensor, the blending ratio is computed by learning on the basis of the feedback from the $O_2$ sensor. However, the blending ratio may not be detected as desired since this feedback learning control is not successfully attained until the driving conditions of the vehicle are more or less stabilized.

SUMMARY OF THE INVENTION

It is an object of the present invention to provide a fuel blending ratio detecting method according to which a memory blending ratio stored at the time of stoppage of an engine can be employed as a control blending ratio when the blending ratio based on the output of a blending ratio sensor and that of an $O_2$ sensor cannot be obtained.

To attain the above object, the present invention provides a system for a fuel blending ratio detecting method comprising a blending ratio sensor for generating information regarding a blending ratio between gasoline and alcohol in fuel supplied to an engine, an $O_2$ sensor for generating information regarding an air/fuel ratio in exhaust gases from said engine, and control means for generating a control blending ratio computed on the basis of the blending ratio information from said blending ratio sensor or the air/fuel ratio information for said $O_2$ sensor. Besides computing said control blending ratio, said control means detects, when said engine is in a backup memory as a memory blending ratio, said memory blending ratio being read for use as said control blending ratio for a predetermined limited period at the time of re-starting said engine.

Thus, according to this method, the control blending ratio under the ordinary engine operating condition is computed on the basis of the output of the blending ratio sensor and that of the $O_2$ sensor, and, when the engine is stopped, the control blending ratio detected at that time is stored in the backup memory as the control blending ratio. As a result, for the predetermined limited period at the time of re-starting the engine, the memory blending ratio can be used as the control blending ratio.

DETAILED DESCRIPTION FOR THE PREFERRED EMBODIMENTS OF THE INVENTION

A fuel blending ratio detecting method according to an embodiment of the present invention will now be described.

Figure 1:
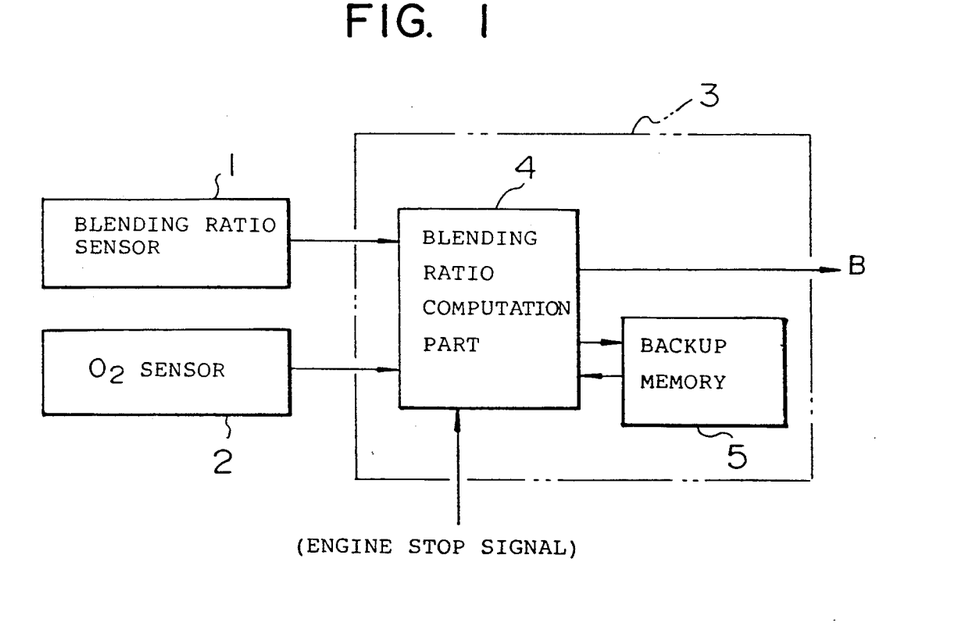
FIG. 1 is a block diagram illustrating the method for an embodiment of the present invention.

As shown in FIG. 1, this method uses a blending ratio sensor 1 generating an output signal $V_{OUT}$ indicating the blending ratio between gasoline and methanol in the fuel supplied to an engine, an $O_2$ sensor 2 capable of generating an output signal $V_O$ indicating the air/fuel ratio in exhaust gases of the engine, a control device 3 for computing a control blending ratio B on the basis of the blending ratio signal $V_{OUT}$ from the blending ratio sensor 1 and the air/fuel ratio signal $V_O$ from the $O_2$ sensor 2.

Figure 5A:
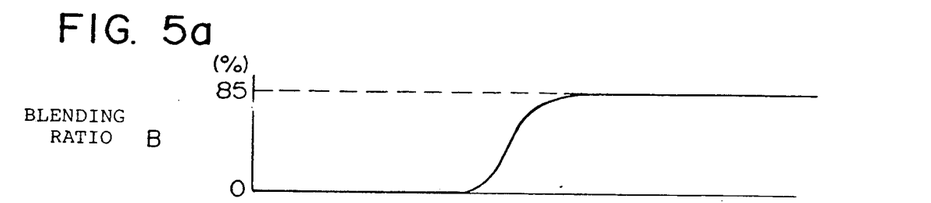
FIGS. 5a to 5e are waveform diagrams showing how the characteristic values in the engine control system shown in FIG. 4 change with time.
Figure 5B:
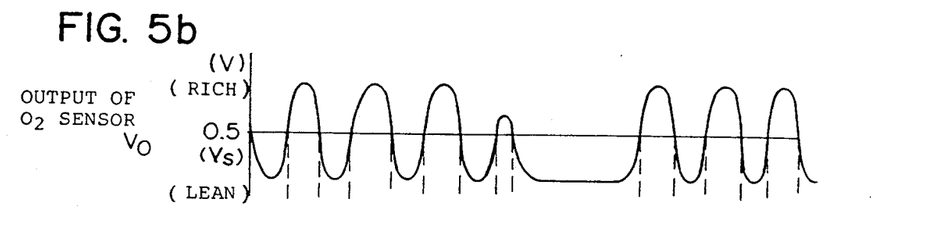

In the method of the present embodiment, the blending ratio signal $V_{OUT}$ indicating the blending ratio of fuel in a fuel feed system is applied to the control device 3 from the blending ratio sensor 1, and the air/fuel ratio signal $V_O$ indicating the air/fuel ratio in the engine exhaust gases is also applied to the control device 3 from the $O_2$ sensor $V_O$ is increased or decreased with time relative to a rich/lean decision voltage $V_S$ (the value where the air/fuel ratio of the exhaust gases is regarded to be stoichiometric). (Refer to FIG. 5b.)

When the engine is normally operating, a blending ratio computation part 4 in the control device 3 computes a blending ratio $B_{FCS}$ according to a predetermined computation processing routine on the basis of the blending ratio signal $V_{OUT}$.

Then, when a predetermined timing is reached, a blending ratio compensation coefficient $K_B$ is computed on the basis of the air/fuel ratio signal $V_O$, and a blending ratio $B_{O2}$, is computed on the basis of this blending ratio compensation coefficient $K_B$. When the blending ratio $B_{O2}$, is already known, that value is used as the control blending ratio B, and when the blending ratio $B_{O2}$ is not already known, the blending ratio $B_{FCS}$ is used as the control blending ratio B.

When the engine is stopped, the control blending ratio B at that time is stored in a backup memory 5 as a memory blending ratio $B_{MEM}$, and at the time of re-starting the engine, this memory blending ratio $B_{MEM}$ is read out to be used as the control blending ratio B for a predetermined limited period.

Thus, when both the $O_2$ sensor 2 and the blending ratio sensor 1 are in their inactive state as when the engine is re-started from its cold condition, the memory blending ratio $B_{MEM}$ is employed and generated as the control blending ratio B. After the predetermined limited period, the blending ratio $B_{O2}$ or the blending ratio $B_{FCS}$ can be employed, so that the reliable control blending ratio B can be always obtained.

Now, an engine control system for an FFV to which the fuel blending ratio detecting method of the present embodiment is applied will be described by reference to FIG. 4.

Figure 4:
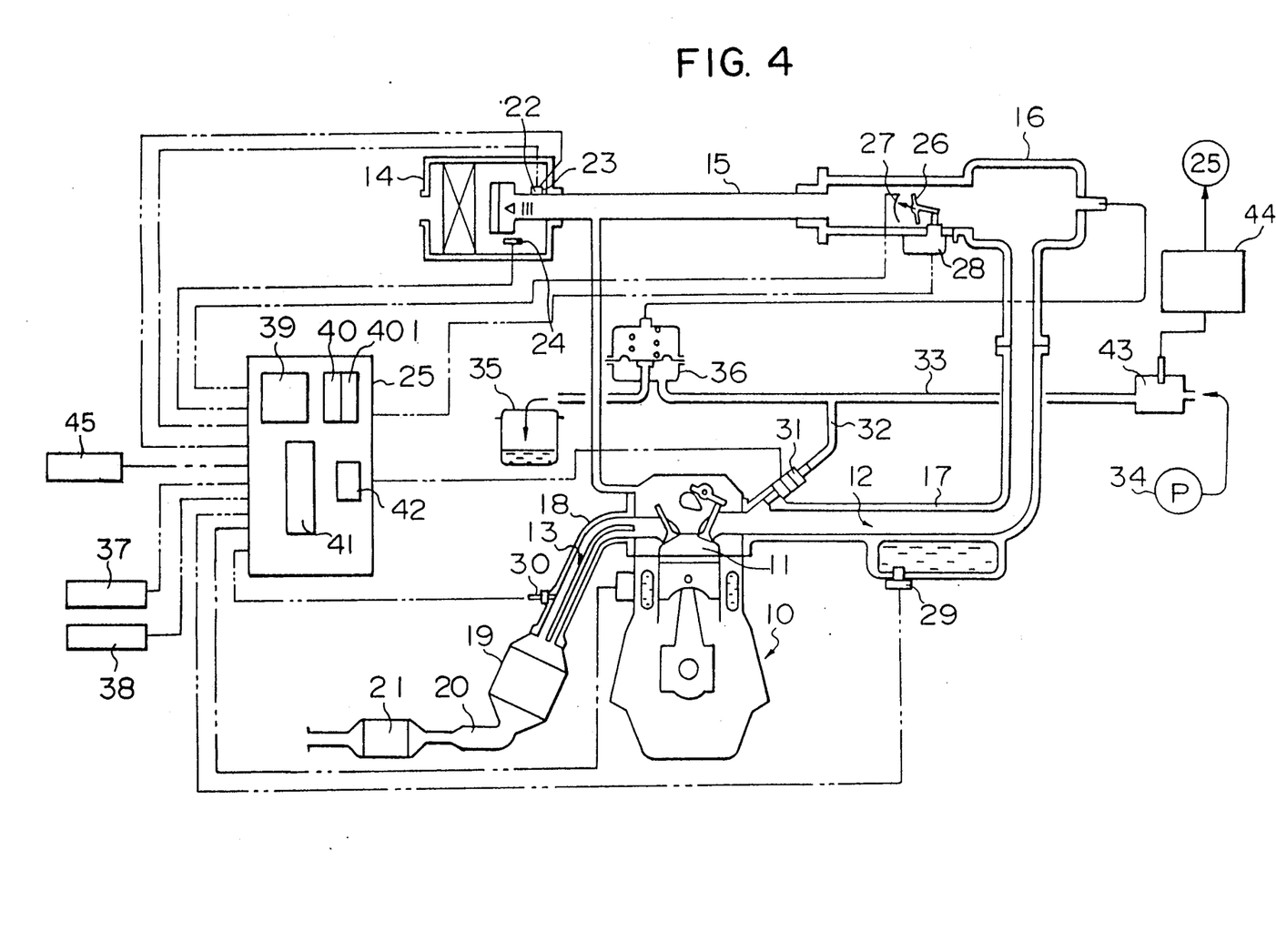
FIG. 4 schematically shows the structure of an engine control system to which the method for an embodiment of the present invention is applied.

Referring to FIG. 4, combustion chambers 11 of an engine 10 communicate with an intake passage 12 and an exhaust passage 13 at suitable times. The intake passage 12 is formed of an air cleaner 14, a first intake pipe 15, an expansion pipe 16, and a second intake pipe 17. The exhaust passage 13 is formed of a first exhaust pipe 18, a catalyst 19, a second exhaust pipe 20 and a muffler 21.

An air flow sensor 22 generating information regarding the quantity of air flow, an atmospheric pressure sensor 23 generating information regarding the atmospheric pressure, and an atmospheric temperature sensor 24 generating information regarding the air temperature are disposed in the air cleaner 14, and they are connected to an engine control unit (referred to hereinafter merely as a controller) 25.

A throttle valve 26 is mounted in the expansion pipe 16, and a throttle position sensor 27 is associated with the throttle valve 26. The idle position of this throttle valve 26 is controlled by the controller 25 through an idle speed control motor (an ISC motor) 28.

A water jacket is associated with part of the second intake pipe 17, and a water temperature sensor 29 is mounted on the water jacket.

Midway in the first exhaust pipe 18, an $O_2$ sensor 30 is mounted so as to generate information regarding the air/fuel ratio in the exhaust gases from the engine 10.

Fuel injection valves 31 are mounted at the end of the intake passage 12. Each of these fuel injection valves 31 is connected to a fuel pipe 33 through a branch pipe 32. This fuel pipe 33 connects between a fuel pump 34 and a fuel tank 35, and, midway in this fuel pipe 33, a blending ratio sensor 43 and a fuel pressure regulator 36 for regulating the fuel pressure are mounted.

The blending ratio sensor 43 is connected to the controller 25 through an amplifier 44.

In FIG. 4, the numeral 37 designates a crank angle sensor generating information regarding the crank angle, the numeral 38 designates a top dead center sensor generating information regarding the top dead center of the first cylinder, and the numeral 45 designates a key switch generating an engine on signal.

The controller 25 includes a control circuit 39, a memory circuit 40, an input/output circuit 41, and a valve driver circuit 42.

Figure 6:
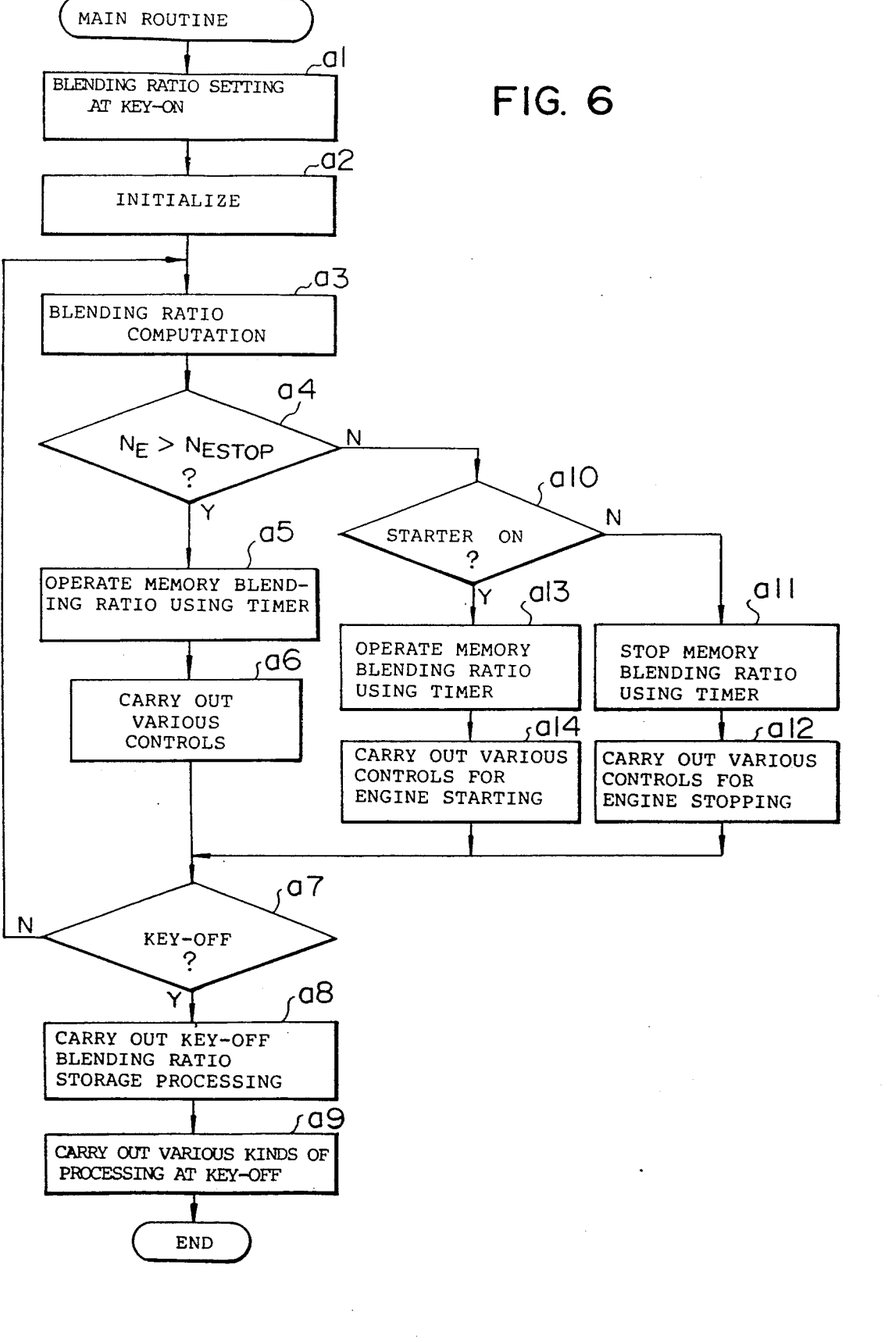
FIGS. 6 to 9 are flow charts of a control program executed by the system shown in FIG. 4 to which the fuel blending ratio detecting method is applied.

The control circuit 39 receives input signals from the individual sensors, and, after processing these input signals according to the control program shown in FIG. 6, etc. generates control signals through the valve driver circuit 42.

The memory circuit 40 stores the control program including a main routine, blending ratio computation, blending ratio setting at the time of key-on and key-off, etc. as shown in FIGS. 6 to 9, together with a blending ratio computation map. (Refer to FIG. 2.) Further, the memory circuit 40 includes an area for storing the blending ratio compensation coefficient $K_B$, the control blending ratio B, and other values. The memory circuit 40 is provided with a non-volatile backup memory 401 which always receives the battery voltage so as to hold these data even at the time of the key-off.

The input/output circuit 41 acts to suitably receive the output signals of the individual sensors described above to generate various control signals through a driver circuit (not shown) or generate a valve drive signal through the valve driver circuit 42 so as to open each of the fuel injection valves 31 at the predetermined timing.

On the other hand, the amplifier 44 forms also part of the microcomputer and generates its detected optical output. At the same time, the amplifier 44 generates the blending ratio signal $V_{OUT}$ on the basis of the photocurrent signal appearing from the blending ratio sensor as a result of photoelectric conversion of refracted light including the blending ratio information.

The operation of the controller 25 will now be described together with the control program shown in FIGS. 6 to 9.

When an engine key switch (not shown) is turned on, the controller 25 and the individual sensors start to operate.

Figure 7:
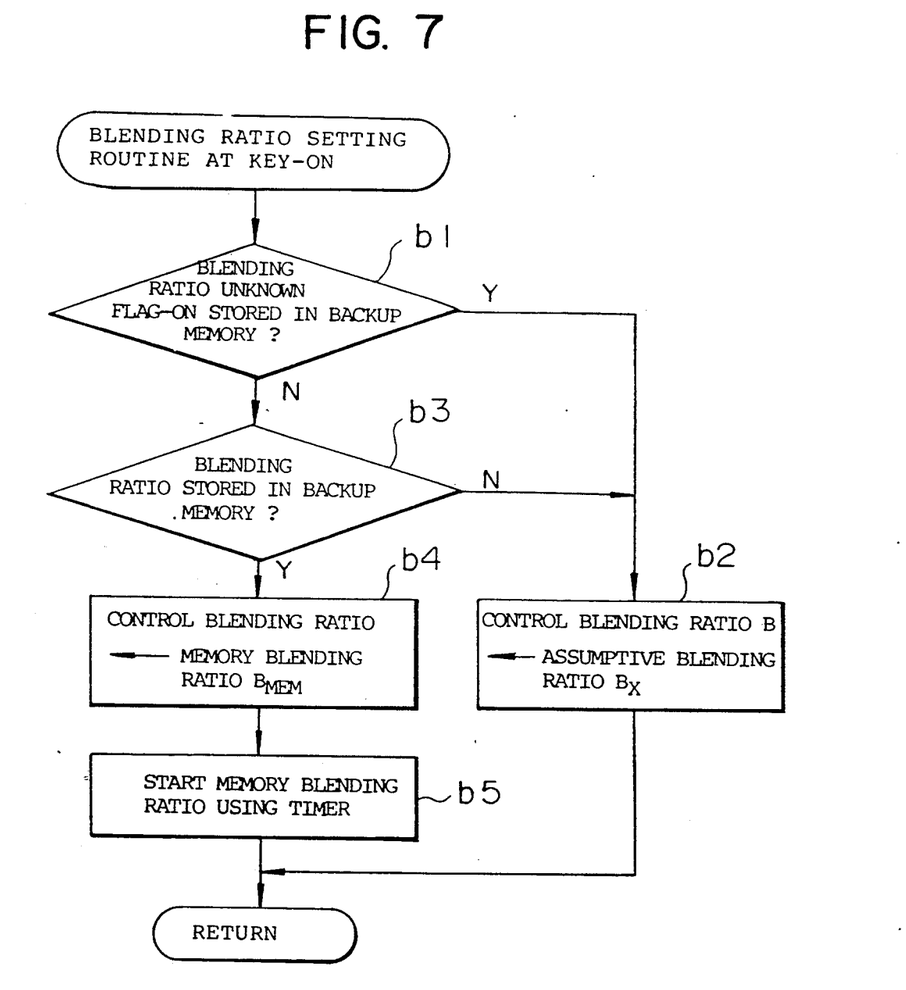

First, in a step a1 of a main routine shown in FIG. 6, the controller 25 executes a routine shown in FIG. 7 for setting the blending ratio at the time of the key-on. In a step b1 in FIG. 7, a decision is made as to whether or not a blending ratio unknown flag-on is stored already in the backup memory 401. When the blending ratio is determined to be unknown, the step b1 is followed by a step b2 in which a pre-set assumptive blending ratio $B_X$ is set as the control blending ratio B. The program then returns.

The pre-set assumptive blending ratio $B_X$ described above is such that the real blending ratio is zero, that is, the value (M=100%) where knocking tends to most frequently occur without causing any trouble of the engine.

On the other hand, when the blending ratio unknown flag-on is not stored, the step b1 is followed by a step b3 in which a decision is made as to whether or not the control blending ratio B is stored already in the backup memory 401. When the control blending ratio B is not stored, the step b3 is followed by the step b2, and when the control blending ratio B is stored, the step b3 is followed by a step b4. In this step b4, the control blending ratio B is computed as a memory blending ratio $B_{MEM}$ and, in a step b5, a memory blending ratio using a timer is started. The program then returns.

When the program returns to a step a2 of the main routine shown in FIG. 6, the controller 25 initializes various settings, measured values, etc. and executes a blending ratio computation routine in a step a3.

Figure 8:
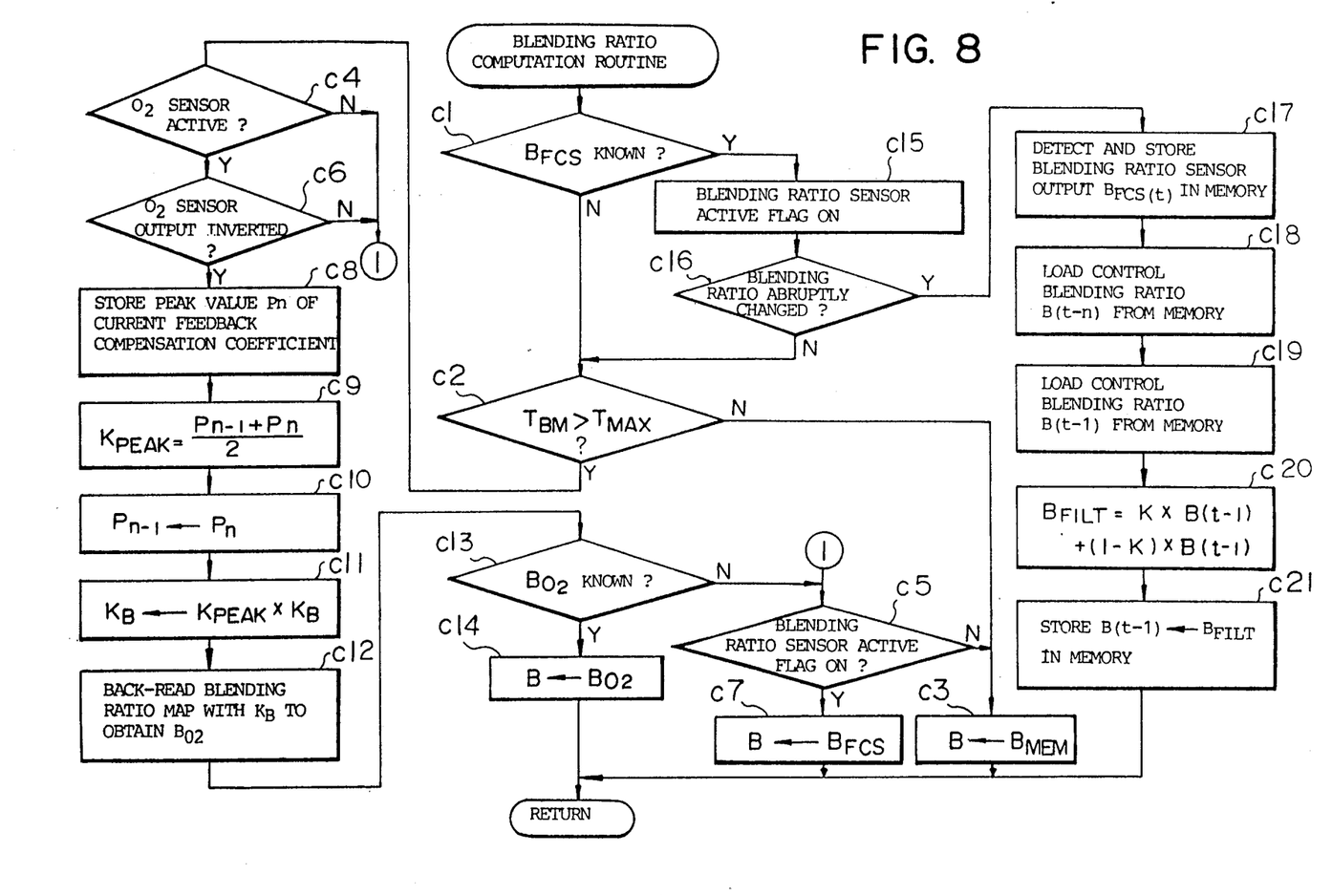

In the blending ratio computation routine shown in FIG. 8, a decision is made in a step c1 as to whether or not the blending ratio $B_{FCS}$ has already been computed in the main routine on the basis of the blending ratio signal $V_{OUT}$ from the amplifier. When this blending ratio $B_{FCS}$ not already known, a decision is made in a step c2 as to whether or not the count of the memory blending ratio using a timer $T_{BM}$ has exceeded $T_{MAX}$, that is, as to whether or not the period using the memory blending ratio $B_{MEM}$ has elapsed. Before the period is elapsed, in a step c3, the memory blending ratio $B_{MEM}$ is used as the control blending ratio B, and the program returns. On the other hand, after the period has elapsed, the step c2 is followed by a step c4.

In this step c4, whether the $O_2$ sensor 30 is active or not is decided on the basis of the following conditions:

1. The $O_2$ sensor 30 is determined to be inactive when the sensor output crosses a predetermined level (for example, 0.6 V) when 15 seconds has elapsed after the engine is stalled and started. 2. The $O_2$ sensor 30 is decided to be inactive when the state where the sensor output does not cross a predetermined level (for example, 0.6 V) continues over a predetermined period (for example, 20 seconds) during the feedback control.

When the $O_2$ sensor 30 is not determined to be active, the step c4 is followed by a step c5. On the other hand, when the $O_2$ sensor 30 is determined to be active, the step c4 is followed by a step c6 which decides whether or not the magnitude relation between the output of the $O_2$ sensor 30 and a decision voltage $V_{Ref}$ is inverted. The preceding sensor output is expressed as $V_{N-1}$, the current sensor output is expressed as $V_N$, and the rich/lean decision voltage is expressed as $V_{Ref}$, and these values are successively updated and stored in the predetermined area. Then, the signs of $(V_{N-1}-V_{Ref})$ and $(V_N-V_{Ref})$ are compared, and, when the signs are different, the magnitude relation is determined to be inverted now.

When the output of the $O_2$ sensor 30 is determined not to be inverted in the step c6, the step c6 is followed by the step c5. On the other hand, when the sensor output is inverted (for example, when the sensor output crosses the rich/lean decision voltage $V_S$ (=0.5 V) shown in FIG. 5b), the step c6 is followed by a step c8.

When the step c5 is reached because the output of the $O_2$ sensor 30 is not inverted, whether the blending ratio sensor 43 is active or not is determined in this step c5. When the blending ratio sensor active flag is on, the blending ratio sensor active flag is on, the blending ratio $B_{FCS}$ detected by the blending ratio sensor is generated as the control blending ratio B, and the program returns.

On the other hand, when the blending ratio sensor 43 is inactive, the memory blending ratio $B_{MEM}$ is selected as the control blending ratio B, and the program returns.

Figure 5C:
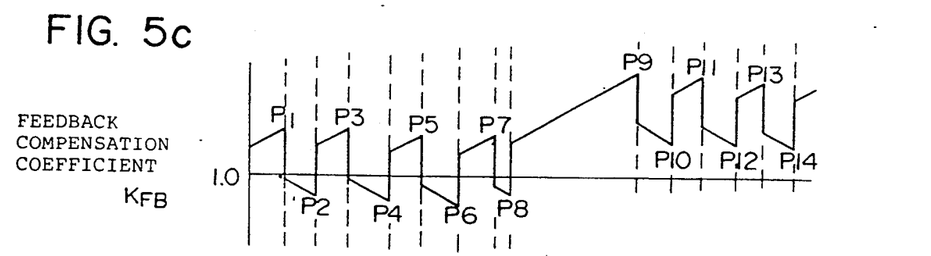

When the step c8 is reached because the output of the $O_2$ sensor 30 is determined as being inverted, peak values $P_n$ (for example, maximum and minimum values $P_1$, $P_2$, $P_3$, ... shown in FIG. 5c) of a feedback compensation coefficient $K_{FB}$ obtained by proportional and integral processing of a proportional gain and an integral gain according to the magnitude relation between the air/fuel ratio indicative output $V_O$ of the $O_2$ sensor 30 and the decision voltage $V_S$ are stored in a predetermined area.

Then, in a step c9, the mean value of the preceding peak value $P_{n-1}$ and the current peak value $P_n$ is computed as the peak mean value $K_{PEAK}[=(P_{n-1}+P_n)/2]$. Then, in a step c10, the peak value $P_n$ is stored in the memory as the preceding peak value $P_{n-1}$.

It is supposed now that the blending ratio B of the fuel is changed from 100% of gasoline to 85% of methanol. (Refer to FIG. 5a.)

In this case, because the stoichiometric air/fuel ratio of the methanol is lower than that of the gasoline (shortage of fuel), the sensor output $V_O$ continues to fluctuate on the lean side. (Refer to FIG. 5b.) Then, the feedback compensation coefficient $K_{FB}$ obtained as described above continues to increase or decrease on the rich side. (Refer to FIG. 5c.)

Figure 5D:
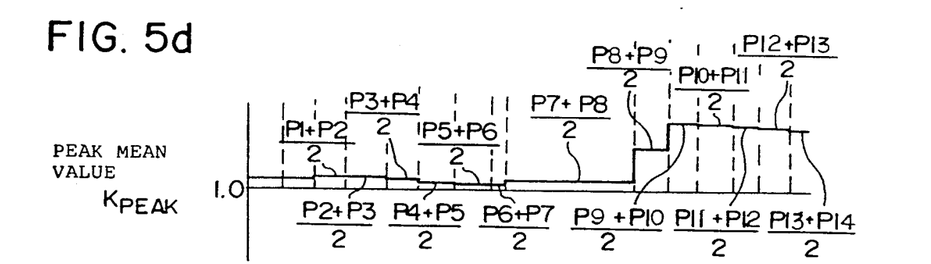
Figure 5E:
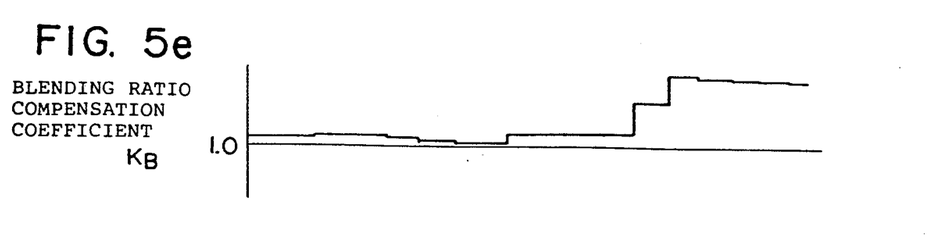

Then, in a step c11, the blending ratio compensation coefficient $K_B$ is read out from the predetermined area, and this value is multiplied by the peak mean value $K_{PEAK}$ so as to update $K_B$ ($K_B \leftarrow K_B \times K_{PEAK}$). (Refer to FIGS. 5d and 5e.)

Figure 2:
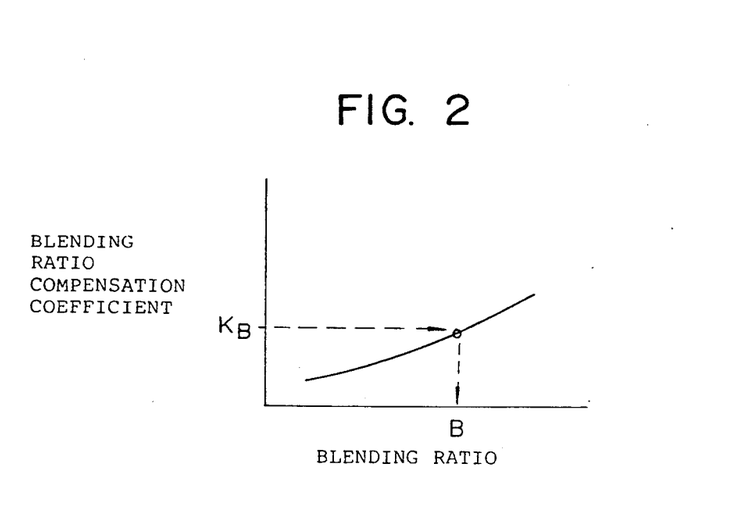
FIG. 2 illustrates a map used in the method for an embodiment of the present invention for computing the blending ratio.

Then, in a step c12, the controller 25 back-reads the blending ratio map (shown in FIG. 2) in a direction as shown by the arrow in FIG. 2 and computes the blending ratio $B_{O2}$ on the basis of the updated blending ratio compensation coefficient $K_B$. The step c12 is followed by a step c13.

In the step c13, a decision is made as to whether or not the blending ratio $B_{O2}$ is already known. When the blending ratio $B_{O2}$ is already known, the step c13 is followed by a step c14 in which the blending ratio $B_{O2}$ is generated as the control blending ratio B. On the other hand, when the blending ratio $B_{O2}$ is unknown, the step c13 is followed by the step c5 in which the blending ratio $B_{FCS}$ or the memory blending ratio $B_{MEM}$ is selected, and the program returns.

The step c1 is followed by a step c15 when the blending ratio $B_{FCS}$ is already known, and the blending ratio sensor active flag-on processing is carried out. Then, in a step c16, a decision is made as to whether or not an abrupt change on the blending ratio has occurred. In this case, the step c16 decides that an abrupt change has occurred when the difference between the current control blending ratio and the preceding control blending ratio exceeds a setting.

Figure 3:
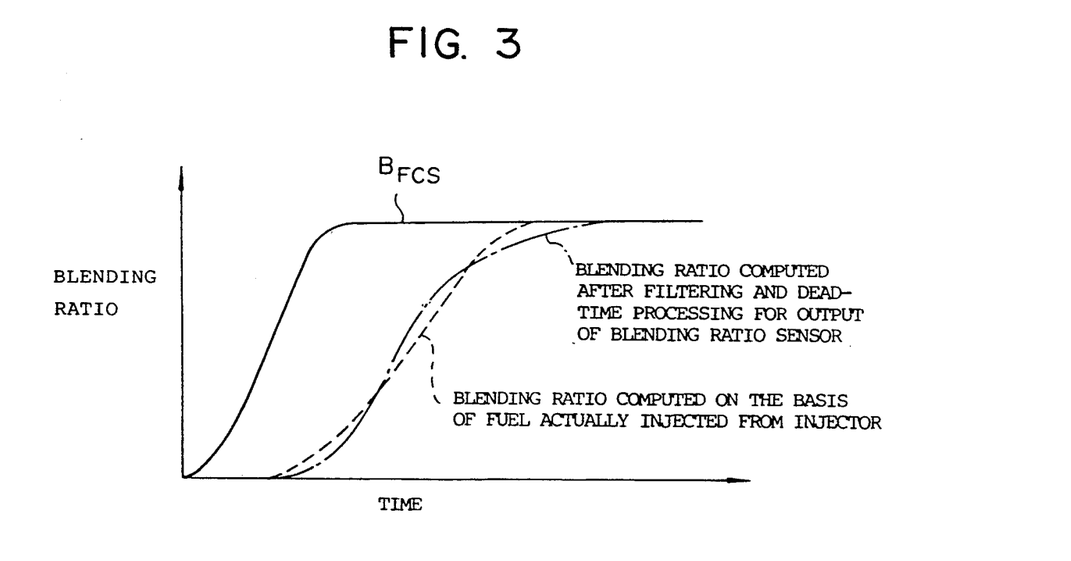
FIG. 3 illustrates deviations between the blending ratio of fuel injected from a fuel injection valve and that computed on the basis of the blending ratio sensor output.

When such an abrupt change is not detected, the step c16 is followed by the step c2, and when the abrupt change is detected, the step c16 is followed by a step c17 to start steps of processing in which deviations of the blending ratio $B_{FCS}$, detected by the blending ratio sensor 43, from the real blending ratio (FIG. 3) due to the capacities of the fuel injection valves (injectors) 31 and the blending ratio sensor 43 are compensated.

In the step c17, the blending ratio $B_{FCS}$ from the blending ratio sensor 43 is stored in a predetermined area of the memory. Then, in a step c18, the control blending ratio $B(t-n)$ used n times before is loaded from the memory, and, in a step c19, the preceding control blending ratio $B(t-1)$ is loaded from the memory.

Then, in a step c20, the predetermined filter coefficient K, the dead time n due to delay of the fuel feed, the preceding control blending ratio $B(t-1)$ and the control blending ratio $B(t-n)$ detected n times before are loaded, and, on the basis of these values, the current filter blending ratio $B_{FILT}$ is computed according to the following equation:

$$B_{FILT} = K \times B(t-1) + (1-K) \times B.$$

Thereafter, in a step c21, the preceding control blending ratio $B(t-1)$ is updated by the current filter blending ratio $B_{FILT}$, and the program returns.

After the blending ratio computation routine is executed, the program returns to a step a4 of the main routine shown in FIG. 6. In this step a4, the engine rotation speed $N_E$ is detected, and a decision is made as to whether or not the detected engine rotation speed $N_E$ is higher than an engine operation decision speed $N_{ESTOP}$.

When a step a5 is reached during the operation of the engine 10, the memory blending ratio using a timer is operated, and the step a5 is followed by a step a6. In this step a6, the control blending ratio B and the blending ratio compensation coefficient $K_B$ are suitably read out so as to carry out processing for controlling the quantity of fuel injection and to compute also the blending ratio $B_{FCS}$ on the basis of the blending ratio signal $V_{OUT}$. After execution of other controls, the step a6 is followed by a step a7.

For example, in the step a6, the fuel injection valve driving time $T_{inj}$ is computed. First, the basic driving time $T_B[=(A/N(n)\times K_B\times K]$ per unit intake air quantity is computed. This blending ratio compensation coefficient $K_B$ is used so that the basic driving time $T_B$ (the basic fuel quantity) per predetermined intake air quantity $A/N(n)$ can be regulated to the value corresponding to the blending ratio of the supplied fuel. In the above expression, k is another compensation coefficient. Then, the fuel injection valve driving time $T_{inj}$ is computed using the basic driving time $T_B$, the feedback compensation coefficient $K_{FB}$ and compensated values of the atmospheric air temperature compensation coefficient Kt, atmospheric pressure compensation coefficient Kb, water temperature compensation coefficient Kwt and acceleration compensation coefficient Kac. ($T_{inj}=T_B\times K_{FB}\times Kt\times Kb\times Kwt\times Kac$).

When the step a7 is reached, a decision is made as to whether or not the key is off. When the key is not off, the step a7 is followed by the step a3, while when the key is off, the step a7 is followed by a step a8 in which a blending ratio storage routine at the key-off shown in FIG. 9 is executed.

Figure 9:
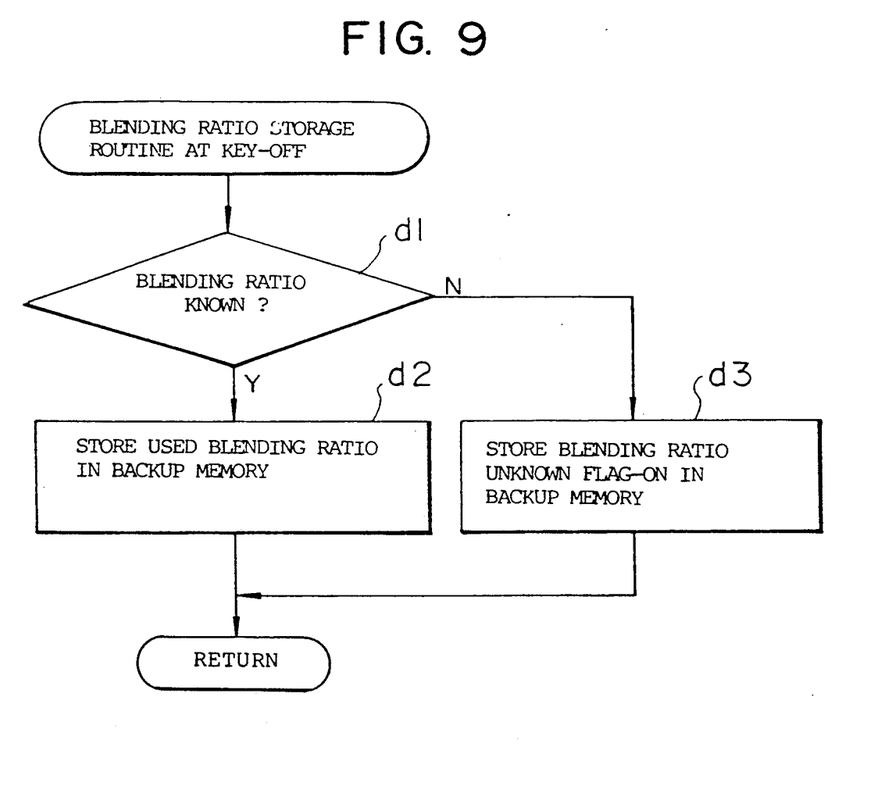

As shown in FIG. 9, in a step d1, a decision is made as to whether or not the control blending ratio B is already known. When this control blending ratio B is already known, the step d1 is followed by a step d2 in which the control blending ratio B now in use is stored in the backup memory 401 as the memory blending ratio $B_{MEM}$. On the other hand, when this control blending ratio B is unknown, the step d1 is followed by a step d3 in which a blending ratio unknown flag-on is stored in the backup memory 401, and the program returns.

When the program returns to a step a9 of the main routine shown in FIG. 6, various kinds of processing required at the time of the key-off are finally executed.

When the step a4 decides that the engine 10 is stopped, the step a4 is followed by a step a10 in which it is checked whether the starter switch is on or not. When the starter switch is off, the step a10 is followed by a step a11. In this step a11, the memory blending ratio using a timer continue to be stopped, and, in a step a12, a required processing to deal with the engine stoppage is carried out. Then, the step a12 is followed by the step a7.

On the other hand, when the starter switch is on, the step a10 is followed by a step a13. In this step a13, the memory blending ratio using a timer is operated, and, in a step a14, various kinds of processing to deal with engine starting are carried out. Then, the step a14 is followed by the step a7.

Thus, according to the fuel blending ratio detecting method carried out by the engine control system shown in FIG. 4, the blending ratio $B_{O2}$ detected by the $O_2$ sensor 30 is used as the control blending ratio B when the blending ratio $B_{O2}$ is already known, while the blending ratio $B_{FCS}$ detected by the blending ratio sensor is used as the control blending ratio B when the blending ratio $B_{O2}$ is unknown. When the latter blending ratio $B_{FCS}$ is also not already known, the memory blending ratio $B_{MEM}$ which is an assumptive blending ratio $B_X$ can be used as the control blending ratio B, or this memory blending ratio $B_{MEM}$ can be generated as the control blending ratio B when the memory blending ratio using timer $T_{MB}$ is operating. Further, when the blending ratio is abruptly changed, the filter blending ratio $B_{FILT}$ filtered so as to compensate blending ratio deviations between the blending ratio sensor 43 and the fuel injection valves 31 can be generated as the control blending ratio B, so that the blending ratio having a high reliability can be generated throughout the operation range of the engine.

It will be understood from the foregoing description that, in the method according to the present invention, the control blending ratio B under the ordinary operating condition of the engine 10 is computed on the basis of the output of the blending ratio sensor 1 and that of the $O_2$ sensor 2, and, when the engine 10 is stopped, the control blending ratio B at that time is stored in a backup memory 5 as a memory blending ratio $B_{MEM}$, so that, for a predetermined limited period at the time of re-starting the engine, the memory blending ratio $B_{MEM}$ can be used as the control blending ratio B. Therefore, the blending ratio can be detected with a high reliability.

We claim:

1. A fuel blending ratio detecting method characterized in that a blending ratio sensor generating information regarding the blending ratio between gasoline and alcohol in fuel supplied to an engine, an $O_2$ sensor generating information regarding the air/fuel ratio in exhaust gases from said engine, and control means generating a control blending ratio computed on the basis of said blending ratio information from said blending ratio sensor or said air/fuel ratio information are used, and, besides computing said control blending ratio, said control means reads, when said engine is stopped, the blending ratio detected at that time to store it in a backup memory as a memory blending ratio, said memory blending ratio being generated as the control blending ratio for a predetermined limited period at the time of re-starting said engine.

* * * * *